US005874440A

United States Patent [19]
Pamukcu et al.

[11] Patent Number: 5,874,440
[45] Date of Patent: Feb. 23, 1999

[54] METHOD OF TREATING A PATIENT HAVING PRECANCEROUS LESIONS WITH PHENYL PYRIMIDINONE DERIVATIVES

[75] Inventors: Rifat Pamukcu, Spring House, Pa.; Gary Piazza, Highlands Ranch, Colo.

[73] Assignee: Cell Pathways, Inc., Aurora, Colo.

[21] Appl. No.: 472,854

[22] Filed: Jun. 7, 1995

[51] Int. Cl.⁶ .................................................. A61K 31/505
[52] U.S. Cl. ........................................................ 514/269
[58] Field of Search .......................................... 514/269

[56] References Cited

U.S. PATENT DOCUMENTS

| | | | |
|---|---|---|---|
| 3,031,450 | 4/1962 | Fischer et al. | 260/247.5 |
| 3,161,654 | 12/1964 | Shen | 260/319 |
| 3,322,755 | 5/1967 | Roch et al. | 260/246 |
| 3,517,005 | 6/1970 | Cronin et al. | 260/256.4 |
| 3,594,480 | 7/1971 | Cronin et al. | 424/251 |
| 3,647,858 | 3/1972 | Hinkley et al. | 260/470 |
| 3,654,349 | 4/1972 | Shen et al. | 260/515 |
| 3,780,040 | 12/1973 | Schnettler et al. | 260/256.5 |
| 3,812,127 | 5/1974 | Cronin et al. | 260/268 BQ |
| 3,819,631 | 6/1974 | Broughton et al. | 260/256.4 F |
| 3,920,636 | 11/1975 | Takahasi et al. | 260/240 J |
| 4,001,237 | 1/1977 | Partyka et al. | 260/256.4 |
| 4,001,238 | 1/1977 | Partyka et al. | 260/256.4 B |
| 4,039,544 | 8/1977 | Broughton et al. | 424/251 |
| 4,060,615 | 11/1977 | Matier et al. | 434/251 |
| 4,079,057 | 3/1978 | Juby et al. | 424/251 |
| 4,098,788 | 7/1978 | Crenshaw et al. | 544/293 |
| 4,101,548 | 7/1978 | Crenshaw et al. | 544/284 |
| 4,102,885 | 7/1978 | Crenshaw et al. | 544/286 |
| 4,138,561 | 2/1979 | Crenshaw et al. | 544/284 |
| 4,146,718 | 3/1979 | Jenks et al. | 544/292 |
| 4,161,595 | 7/1979 | Kaplan et al. | 544/284 |
| 4,171,363 | 10/1979 | Crenshaw et al. | 424/251 |
| 4,208,521 | 6/1980 | Crenshaw et al. | 544/250 |
| 4,209,623 | 6/1980 | Juby | 544/319 |
| 4,423,075 | 12/1983 | Dvornik et al. | 424/317 |
| 4,460,590 | 7/1984 | Möller | 424/251 |
| 4,460,591 | 7/1984 | DeGraw et al. | 424/251 |
| 4,880,810 | 11/1989 | Lowe, III et al. | 514/258 |
| 4,885,301 | 12/1989 | Coates | 514/263 |
| 4,923,874 | 5/1990 | McMahon et al. | 514/258 |
| 5,073,559 | 12/1991 | Coates | 514/262 |
| 5,147,875 | 9/1992 | Coates et al. | 514/259 |
| 5,223,501 | 6/1993 | Chakravarty et al. | 514/258 |
| 5,250,535 | 10/1993 | Verheyden et al. | 514/262 |
| 5,254,571 | 10/1993 | Coates et al. | 514/345 |
| 5,358,952 | 10/1994 | Moschel et al. | 514/262 |
| 5,401,774 | 3/1995 | Pamukcu et al. | 514/569 |
| 5,439,895 | 8/1995 | Lee et al. | 514/63 |
| 5,614,530 | 3/1997 | Kumar et al. | 514/293 |
| 5,614,627 | 3/1997 | Takase et al. | 544/293 |

FOREIGN PATENT DOCUMENTS

| | | |
|---|---|---|
| 0 347146 A2 | 12/1989 | European Pat. Off. . |
| 0 349239 A2 | 1/1990 | European Pat. Off. . |
| 0 351058 | 1/1990 | European Pat. Off. . |
| 0 352960 A2 | 1/1990 | European Pat. Off. . |
| 0 395328 A2 | 10/1990 | European Pat. Off. . |
| 0 428268 A2 | 5/1991 | European Pat. Off. . |
| 0 463756 A1 | 1/1992 | European Pat. Off. . |
| 0 485157 A2 | 5/1992 | European Pat. Off. . |
| 0 485158 A2 | 5/1992 | European Pat. Off. . |
| 0 485171 A2 | 5/1992 | European Pat. Off. . |
| 0 485172 A2 | 5/1992 | European Pat. Off. . |
| 0 485173 A2 | 5/1992 | European Pat. Off. . |
| 0 508586 A1 | 10/1992 | European Pat. Off. . |
| 0 526004 A1 | 2/1993 | European Pat. Off. . |
| 0 607439 A1 | 7/1994 | European Pat. Off. . |
| 56-53659 A | 5/1981 | Japan . |
| 57-167974 A | 10/1982 | Japan . |
| 807826 | 1/1959 | United Kingdom . |
| 2063249 | 6/1981 | United Kingdom . |
| WO 92/03419 | 3/1992 | WIPO . |
| WO 93/07149 | 4/1993 | WIPO . |
| WO 93/12095 | 6/1993 | WIPO . |
| WO 94/05661 | 3/1994 | WIPO . |
| WO 97/03985 | 2/1997 | WIPO . |

OTHER PUBLICATIONS

Biddle, William et al., Antineoplastic Effect of the Pyrimido–Pyrimidine Derivative: RA 233, Pathologie Biologie, Jan. 1984, pp. 9–13.

Mehta, Rajendra et al., Structure–Activity Relationships of Brassinin in Preventing the Development of Carcinogen–Induced Mammary Lesions in Organ Culture, Anticancer Research 14: 1209–1214 (1994).

Makaryan, A.P., et al., *Laboratornoe Delo*, "Cyclic Nucleotides In Patients With Malignant Neoplasms Of The Colon–",vol. 8, pp. 31–33 (1991).

Waddell, W.R. et al., Am. J. Surgery, vol. 157, pp. 175–179 (1989).

Gonzaga, R.A.F. et al., The Lancet, Mar. 30, 1985, p. 751.

Waddell, W.R. et al., J. Surg. Oncology, vol. 24, pp. 83–87 (1983).

Federation Proceedings (1972) of the Federation of American Societies for Experimental Biology abstract Nos. 2044 and 2045.

Gilman, S.C. et al., Nonsteroidal Anti–inflammatory Drugs in Cancer Therapy, (circa 1985).

Brogden, R.N. et al., Drugs, vol. 16, pp. 97–114 (1978).

Hucker, H.B. et al., Drug Metabolism & Disposition, vol. 1, No. 6, pp. 721–736 (1973).

Shen, T.Y. et al., Chemical and Biological Studies on Indomethacin, Sulindac and Their Analogs, pp. 107–178 (circa 1975).

Duggan, D.E. et al., Clin. Pharm. & Therapeutics, vol. 21, No. 3, pp. 326–335 (1976).

Duggan, D.E. et al., J. Pharm. & Exper. Therap., vol. 201, No. 1, pp. 8–13 (1977).

Glavin, G.B. et al., Toxicology and Applied Pharmacology, vol. 83, pp. 386–389 (1986).

Moorghen, M. et al., Journal of Pathology, vol. 156, pp. 341–347 (1988).

(List continued on next page.)

*Primary Examiner*—Jerome D. Goldberg
*Attorney, Agent, or Firm*—Brinks Hofer Gilson & Lione

[57] ABSTRACT

Derivatives of Phenyl Pyrimidinone are useful for the treatment of patients having precancerous lesions. These compounds are also useful to inhibit growth of neoplastic cells.

16 Claims, No Drawings

OTHER PUBLICATIONS

Moorghen, M. et al., Acta Histochemica, Suppl.–Band XXIX, S. 195–199 (1990).

Bjarnason et al., Gastroenterology, vol. 94, No. 4, pp. 1070–1074 (1988).

Badrieh, Y., et al., Chem. Ber., vol. 125, pp. 667–674 (1992).

Silvola, J. et al., Effects of nonsteroidal anti–inflammatory drugs on rat gastric mucosal phosphodiesterase activity, Agents and Actions, vol. 12.4, pp. 516–520 (1982).

Curtis–Prior, P.B. et al., Cyclic Nucleotide Phosphodiesterase Activity of Human Normal and Carcinomatous Lung Tissue, The Lancet, pp. 1225–1225 Dec. 4, 1976.

Pepin, P. et al., Effects of Sulindac and Oltipraz on the tumorigenicity of 4–(methylnitrosamino)1–(3–pyridyl)–1–Butanone in A/J mouse lung, Carcinogenesis, vol. 13, No. 3, pp. 341–348 (1992).

Nicholson, C.D. et al. Differential modulation of tissue function and therapeutic potential of selective inhibitors of cyclic nucleotide phosphodiesterase isoenzymes, Trends Pharmacol. Sci. (TiPS), vol. 12, pp. 19–27 (1991).

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Luginer, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Turner, N.C. et al., Relaxation of guinea–pig trachea by cyclic AMP phosphodiesterase inhibitors and their enhancement by sodium mitroprusside, Br. J. Pharmacol. vol. III, pp. 1047–1052 (1994).

Weishaar, R.E. et al., Multiple Molecular Forms of Cyclic Nucleotide Phosphodiesterase in Cardiac and Smooth Muscle and In Platelets, Biochem. Pharmacology, vol 35, No. 5, pp. 787–800 (1986).

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

Saeki, T. et al., Isolation of Cyclic Nucleotide Phosphodiesterase Isozymes From Pig Aorta, Biochem. Pharmacology, vol. 46, No. 5, pp. 833–839 (1993).

Turner, N.C. et al., Pulmonary effects of type V cyclic GMP specific phosphodiesterase inhibition in anaesthetized guinea–pig, Br. J. Pharmacol., vol. 111, 1198–1204 (1994).

Ferreira, S.H. et al., The molecular mechanism of action of peripheral morphone analgesia: stimulation of the cGMP system via nitric oxide release, European Journal of Pharmacology, 201 pp. 121–122 (1991).

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Tulshian, D. et al., Synthesis and Phosphodiesterase Activity of Carboxylic Acid Mimetics of Cyclic Guanosine 3",5"–Monophosphate, J. Med. Chem, vol. 36, 1210–1220 (1993).

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073,2081 (1992).

Broughton, B.J. et al., Antiallergic Activity of 2–Phenyl–8–azapruin–6–ones, Journal of Medicinal Chemistry, vol. 18, No. 11, pp. 1117–1118 (1975).

Kodama, K. et al., Effects of a novel, selective and potent phosphodiesterase type V inhibitor, E4021, on myocardial ischemia in guinea pigs, Euro. J. of Pharma. 263, pp. 93–99 (1994).

Zacharski, L. R. et al., Effect of Mopidamol on Survival in Carcinoma of the Lung and Colon: Final Report of Veterans Administration Cooperative Study No. 188, J. of the Nat'l. Cancer Inst., vol. 80, No. 2, pp. 90–96 (1988).

Lichtner, R. B. et al., The Pyrimido–pyrimidine Derivatives RA 233 adn RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Janik, P. et al., Inhibition of Growth of Primary and Metastatic Lewis Lung Carcinonma Cells by the Phosphodiesterase Inhibitor Isobutylmethylxanthine, Cancer Res. vol. 40, pp. 1950–1954, (Jun. 1980).

Bergstrand, Hakan et al., Effects of Antiallergic Agents, Compound 48/80, and Some Reference Inhibitors on the Activity of Partially Purified Human Lung Tissue Adenosine Cyclic 3',5'–Monophosphate and Guanosine Cyclic 3',5'–Monophosphate Phosphodiesterases, Molecular Pharmacology, 13, pp. 38–43 (1976).

Drees, Markus et al., 3',5'–Cyclic Nucleotide Phosphodiesterase in Tumor Cells as Potential Target for Tumor Growth Inhibition, Cancer Research 53, pp. 3058–3061 (1993).

Semmler, J. et al., Xanthine derivatives: comparison between suppression of tumor necrosis factor–x production and inhibition of cAMP phosphodiesterase activity, Immunology 78, pp. 520–525 (1993).

Clarke, W.R. et al., The type III phosphodiesterase inhibitor milrinone and type V PDE inhibitor dipyridamole individually and synergistically reduce elevated pulmonary vascular resistance (Abstract Only), Pulm. Pharmacol., 7(2), pp. 81–89, (1994).

Raeburn, David et al., Effects of isoenzyme–selective inhibitors of cyclic nucleotide phosphodiesterase on microvascular leak in guinea pig airways in vivo (Abstract Only), J. Pharmacol. Exp. Ther., 267(3), pp. 1147–1151 (1993).

Marcoz, P. et al., Modulation of rat thymocyte proliferative response through the inhibition of different cyclic nucleotide phosphodiesterase isoforms by means of selective inhibitors and cGMP–elevating agents (Abstract Only), Mol. Pharmacol. 44(5) pp. 1027–1035 (1993).

Barnett, Mary S. et al., Initial biochemical and functional characterization of cyclic nucleotide phosphodiesterase isozymes in canine colonic smooth muscle (Abstract Only), J. Pharmacol. Exp. Ther., 264(2) pp. 801–812 (1993).

Molnar–Kimber, K. et al., Modulation of TNFa and IL–1B from indotoxin–stimulated monocytes by selective PDE isozyme inhibitors (Abstract Only), Agents Actions 39(Spec. Conf. Issue), C77–C79 (1993).

Giorgi, Mauro et al., Characterization of 3':5' cyclic nucleotide phosphodiesterase activities of mouse neuroblastoma N18TG2 cells (Abstract Only), FEBS Lett. 324(1) pp. 76–80 (1993).

Porter, Roderick et al., Preparation of 6–phenyl–3–(5–tetrazoly) pyridin–2(H)–one derivatives as cyclic AMP–dependent protein kinase agonists (Abstract Only), PCT Int. Appl. WO9206085 A1, (Sep. 26, 1991).

Molnar–Kimber, K. L. et al., Differential regulation of TNF–a and IL–1B production from endotoxin stimulated human monocytes by phosphodiesterase inhibitors (Abstract Only), Mediators Inflammation 1(6) pp. 411–417 (1992).

Radomski, Marek W. et al., Human Colorectal adenocarcinoma cells: differential nitric oxide synthesis determines their ability of aggregate platelets (Abstract Only), Cancer Res. 51(22) pp. 6073–6078 (1991).

Anderson, Thomas L. G. et al., Interactions between isoprenaline, sodium nitroprusside, and isozyme–selective phosphodiesterase inhibitors on ADP–induced aggretation and cyclic Nucleotide levels in human platelets (Abstract Only), J. Cardiovasc. Pharmacol. 18(2) pp. 237–242 (1991).

Souness, John E. et al., Role of Selective cyclic GMP phosphodiesterase inhibition in the myorelaxant actions of M&B 22,943, MY–5445, vinpocetine and 1–methyl–3–isobutyl–8–(methylamino)xanthine (Abstract Only), Br. J. Pharmacol. 98(3) pp. 725–734 (1989).

Lichtner, Rosemarie B., The pyrimidopyrimidine derivatives RA233 and RX–RA85 affect cell cycle distribution of two murine tumor cell lines (Abstract Only), Eur. J. Cancer Clin. Oncol. 25(6), pp. 945–951 (1989).

Mamytbekova, A., et al., Antimetastatic effect of flurbiprofen and other platelet aggregation inhibitors (Abstract Only), Neoplasma 33(4), pp. 417–421 (1986).

Hagiwara, Masatoshi et al., Effect of 1–(3–chloroanilino)–4–phenylpthalazine (MY–5445), a specific inhibitor of cyclic CMP phosphodiesterase, on human platelet aggregation (Abstract Only), J. Pharmacol. Exp. Ther. 229(2) pp. 467–471 (1984).

Carter et al, Chemotherapy Of Cancer, 2nd ED, John Wiley + Sons, NY,NY, (1981) pp. 362–365.

METHOD OF TREATING A PATIENT HAVING PRECANCEROUS LESIONS WITH PHENYL PYRIMIDINONE DERIVATIVES

TECHNICAL FIELD

This invention relates to methods for treatment or prevention of precancerous lesions.

BACKGROUND OF THE INVENTION

Each year in the United States alone, untold numbers of people develop precancerous lesions. These lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds which prevent or induce the remission of existing precancerous or cancerous lesions or carcinomas would greatly reduce illness and death from cancer.

Approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

As indicated above, each polyp carries with it a chance that it will develop into a cancer. The likelihood of cancer is diminished if a polyp is removed. However, many of these patients demonstrate a propensity for developing additional polyps in the future. They must, therefore, be monitored periodically for the rest of their lives for polyp reoccurrence.

In most cases (i.e. the cases of so-called common sporadic polyps), polyp removal will be effective to reduce the risk of cancer. In a small percentage of cases (i.e. the cases of the so-called polyposis syndromes), removal of all or part of the colon is indicated. The difference between common sporadic polyps and polyposis syndromes is dramatic. Common sporadic polyp cases are characterized by relatively few polyps, each of which can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each polyp carriers with it the palpable risk of cancerous development, polyposis syndrome patients invariably develop cancer if left untreated. Surgical removal of the colon is the conventional treatment. Many of these patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because therapy is often not effective and has severe side effects. Cancer prevention is important for recovered cancer patients who retain a risk of cancer reoccurrence. Also, cancer prevention is important for people who have not yet had cancer, but have hereditary factors that place them at risk of developing cancer. With the development of new diagnostic screening technologies, it is possible to identify those with high risk factors, such as the potential for polyposis syndrome, who would greatly benefit from chemopreventive drugs. Therefore, finding such anti-cancer drugs that can be used for prolonged preventive use is of vital interest to many people.

One way to find such drugs is to screen thousands of compounds for the same biological activity found in known chemopreventive and chemotherapeutic drugs. Most such drugs are now believed to kill cancer cells by inducing apoptosis, or as sometimes referred to as "programmed cell death." Apoptosis naturally occurs in virtually all tissues of the body, and especially in self-renewing tissues such as bone marrow, gut, and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis plays a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long term use, or use in otherwise healthy individuals with precancerous lesions. These side effects, which are a result of the high levels of cytotoxicity of the drugs, include hair loss, weight loss, vomiting and bone marrow immune suppression. Therefore, there is a need to identify new drug candidates for therapy that do not have such serious side effects in humans.

SUMMARY OF THE INVENTION

This invention is a method of treating patients with precancerous lesions or neoplasms by administering a pharmacologically effective amount of a compound of Formula I below to a patient in need of such treatment. Such compositions are effective in modulating apoptosis, and eliminating and inhibiting precancerous lesions, and neoplastic cells.

DETAILED DESCRIPTION OF THE PRESENTLY PREFERRED EMBODIMENTS

As discussed above, this invention is a method of treating a patient with precancerous lesions or neoplasms by administering a pharmacologically effective amount of the phenyl pyrimidinone derivative represented by the following formula (I), or the pharmacologically acceptable salt thereof;

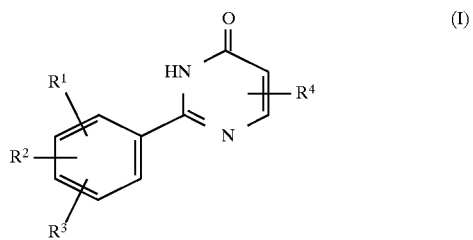

wherein $R^1$, $R^2$ and $R^3$ may be located at any of the available positions on the phenyl ring, each of $R^1$, $R^2$ and $R^3$ may be independently selected from hydrogen, halogen, a lower alkyl group, such as having 1 to 6 carbon atoms, a lower alkoxy, a lower alkenyl, a lower alkenoxy, a lower alkyl thio, a lower alkylamino, a di(lower)alkylamino, a cyano, an acylamino, a carboxyl, a carboalkoxy, a lower alkoxycarbonyl, a lower alkylcarbonyl a cyclo(lower)alkoxy and cyclo(lower)alkyl (lower)alkoxy in which the ring contains 3 to 8 carbon atoms, preferably 3–6 carbon atoms, a phenyl(lower) alkoxy a nitrogen containing ring, a lower alkylcarbamoyloxy, or a halogen substituted lower alkoxy group.

Preferably, $R^1$, $R^2$ and $R^3$ are independently a hydrogen, a halogen, a lower alkyl, a lower alkenyl, a lower alkoxy, a lower alkenyloxy, a phenyl(lower) alkoxy, a cyclo(lower) alkoxy. Preferably, $R^3$ is substituted at position 2 on the phenyl ring, in which case it is preferred that $R^1$ and $R^2$ are hydrogen. More preferably $R^3$ is lower alkoxy, lower alkenoxy, cyclopropylmethoxy or benzoxy. Most preferably $R^3$ is n-propyloxy.

$R^4$ may be a lower alkyl, a lower alkoxy, a phenyl, a hydroxy, a halogen, —NHCOR$^5$, —NHCONHR$^6$, 5-tetrazolyl, —CO$_2$R$^7$, a cyano, —CONR$^8$R$^9$, or —NR$^{10}$R$^{11}$, wherein $R^5$ to $R^9$ are independently hydrogen or lower alkyl or $R^9$ may be 5-tetrazolyl, and $R^{10}$ and $R^{11}$ are independently hydrogen or lower alkyl optionally substituted by hydroxy provided that the carbon atom adjacent to the nitrogen atom is not substituted by hydroxy. Preferably, $R^4$ is a phenyl, a lower alkyl, a hydroxy, a lower alkoxy or —CONR$^8$R$^9$. Preferably, when $R^4$ is positioned on the pyrimidinone ring adjacent the oxygen, $R^4$ is —CONR$^8$R$^9$, in which case, it is preferred that $R^8$ is hydrogen and $R^9$ is 5-1H-tetrazolyl.

"Alkyl group" refers to straight or branched chain $C_1$–$C_{12}$ groups such as methyl, ethyl, propyl, iso-propyl, n-butyl, t-butyl and amyl. "Alkoxy group" refers to hydroxy-substituted alkyl groups such as methoxy, ethoxy, propoxy, butoxy and amyloxy. "Alkoxycarbonyl group" refers to carbonyl-substituted alkoxy groups such as methoxycarbonyl, ethoxycarbonyl, propoxycarbonyl, butoxycarbonyl, amyloxycarbonyl, etc. "Alkylcarbonyl group" refers to carbonyl-substituted alkyl groups such as acetyl, propionyl, butyryl or others. "Halogen" refers to fluorine, chlorine, bromine and iodine. "Lower" refers to 6 or less carbon atoms.

The pharmacologically acceptable salt includes inorganic acid salts such as hydrochloride, hydrobromide, sulfate and phosphate; organic acid salts such as acetate, maleate, tartrate, methanesulfonate, benzenesulfonate and toluenesulfonate; and amino acid salts such as argininate, aspartate and glutamate. Further, some of the compounds may form metal salts such as Na, K, Ca or Mg, and the pharmacologically acceptable salt of formula (I) also includes these metal salts.

Although the compound of formula I may be present as various isomers including geometrical isomers, i.e., cis-isomer and trans-isomer. and optical isomers, i.e., d-isomer and l-isomer depending upon the kinds and combination of the substituents, it is needless to say that the compounds include all of the isomers.

As used herein, the term "precancerous lesion" refers to lesions that exhibit histologic changes which are associated with an increased risk of cancer development. Examples include adenomatous polyps of the colon, dysplastic nevi of the skin and atypical hyperplasia of the breasts. Certain syndromes that commonly display precancerous lesions are also referred to by the term "precancerous" including dysplastic nevus syndrome and the colonic polyposis syndromes. "Precancerous" refers to these lesions or syndromes of various tissues whether or not the lesions are clinically identifiable.

As used herein, the term "carcinomas" refers to lesions which are cancerous. Examples include malignant melanomas, breast cancer, and colon cancer.

As used herein, the term, "neoplasm" refers to both precancerous and cancerous lesions.

As used herein, the term "halo" or "halogen" refers to chloro, bromo, fluoro and iodo groups, and the term "alkyl" refers to straight, branched or cyclic alkyl groups.

Compounds of formula I may be formulated into compositions together with pharmaceutically acceptable carriers for injection, oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g. pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories which may contain, in addition to the compounds of Formula I, excipients such as cocoa butter or a suppository wax.

The pharmaceutically acceptable carrier and compounds of Formula I are formulated into unit dosage forms for administration to a patient. The dosage levels of active ingredient (i.e. compounds of Formula I) in the unit dosage may be varied so as to obtain an amount of active ingredient effective to achieve polyp-eliminating activity in accordance with the desired method of administration (i.e. oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g. two to four times per day.

In another form, the invention is a method of inhibiting the growth of neoplastic cells by exposing them to an effective amount of the compound of formula [I] above.

In still another form, the invention is a method of inducing apoptosis in human cells by exposing those cells to an effective amount of the compound of formula [I] above where such cells are sensitive to this compound.

Additionally, in yet another form, the invention is a method of treating a patient having a disease which would benefit from regulation of apoptosis by treating the patient with an effective amount of the compound of formula [I] above. The regulation of apoptosis is believed to play an important role in diseases associated with abnormalities of cellular growth patterns such as benign prostatic hyperplasia, neurodegenerative diseases such as Parkinson's disease, autoimmune diseases including multiple sclerosis and rheumatoid arthritis, infectious diseases such as AIDS, and other diseases, as well.

The foregoing may be better understood from the following examples, which are presented for purposes of illustration and are not intended to limit the scope of the invention. As used in the following examples, the references to substituents such as R, $R^1$, $R^2$ etc., refer to the corresponding compounds and substituents in the Formula above.

Preferable specific examples of the compound will now be described in order to facilitate the understanding of the present invention, though it is needless to say that the compounds of the present invention are not limited to these examples.

EXAMPLE 1

6-Amino-2-(2-propoxyphenyl)-pyrimidin-4[3H]-one

Ethyl cyanoacetate (4.52 g) was added to a stirred solution of 2-propopoxybenzamidine in ethanol (prepared from sodium, 1.84 g., in ethanol, 100 ml, and 2-propoxybenzamidine methanesulfonate, 11.61 g). The reaction mixture was stirred at ambient temperature for 18 hours and then evaporated under reduced pressure to leave a residue which was dissolved in water. The aqueous solution was extracted with diethyl ether (2×25 ml) and the combined ether extracts were washed with water. The combined aqueous phase was treated with glacial acetic acid to pH 5 to precipitate a crude product. Further crude product was obtained by extracting the ether extracts with 1 normal sodium hydroxide (2×30 ml) and acidifying the combined alkaline extracts with glacial acetic acid to pH 5. The combined crude product was recrystallized from isopropanol to yield the title compound, 2.34 g., m.p. 183.5°–184.5° C.

EXAMPLE 2

6-Acetamido-2-(2-propoxyphenyl)pyrimidin-4[3H]-one

A stirred solution of 6-amino-2-(2-propoxyphenyl) pyrimidin-4[3H]-one (0.5 g) and acetic anhydride (5 ml) was heated under reflux for 2.5 hours. The cooled reaction mixture was evaporated under reduced pressure to yield a residue which was washed with water and recrystallized twice from methanol to yield the title compound, 0.29 g, m.p. 230°–1° C.

EXAMPLE 3

6-Propionamido-2-(2-propoxyphenyl)pyrimidin-4[3H]-one

A stirred solution of 6-amino-2-(2-propoxyphenyl) pyrimidin-4[3H]-one (0.50 g) and propionic anhydride (5 ml) was heated at 140° C. for 2.5 hours. Water and ethanol was added to the cooled reaction mixture which was then evaporated under reduced pressure to half volume. A precipitate was collected, washed with water and recrystallized from ethanol to yield the title compound, 0.41 g, m.p. 228°–90° C.

EXAMPLE 4

6-Butyramido-2-(2-propoxyphenyl)pyrimidin-4[3H]-one

A stirred solution of 6-amino-2-(2-propoxyphenyl) pyrimidin-4[3H]-one (0.68 g) and n-butyric anhydride (7 ml) was heated at 140° C. for 5 hours. Ethanol was added to the cooled reaction mixture which was then evaporated under reduced pressure to yield a residue which was azeotroped and washed with water. The residue was eluted from silica with chloroform and the combined fractions containing product were evaporated under reduced pressure to yield a crude product which was recrystallized from isopropanol:diethyl ether to yield the title compound, 0.21 g, m.p. 177°–80° C.

EXAMPLE 5

6-N-Methylureido-2-(2-propoxyphenyl)pyrimidin-4[3H]-one

A stirred solution of 6-amino-2-(2-propoxyphenyl) pyrimidin-4[3H]-one (0.61 g) and methyl isocyanate (0.14 g) in dioxan was heated under reflux for 3 hours. A second quantity of methyl isocyanate (0.14 g) was added and the reaction mixture was heated under reflux for a further 2 hours. A third quantity of methyl isocyanate (0.28 g) was added and the reaction mixture was heated under reflux for 16 hours. A final quantity of methyl isocyanate (0.28 g) was added and stirring under reflux continued for 7 more hours.

The cooled reaction mixture was evaporated under reduced pressure to yield a crude product which was purified by using column chromatography and by recrystallisation from methanol to yield the title compound, 0.18 g, m.p. 234°–5° C.

EXAMPLE 6

4,6-Dihydroxy-2-(2-propoxyphenyl)pyrimidine

A stirred mixture of diethyl malonate (17.62 g), 2-propoxybenzamidine methanesulfonate (29.03 g) and sodium ethoxide in ethanol (from sodium, 6.9 g, and ethanol, 150 ml) was heated under reflux for 6 hours. The cooled reaction mixture was evaporated under reduced pressure to yield a residue which was dissolved in water. Concentrated hydrochloric acid was added to the aqueous solution to yield the title compound, 21.56 g. A sample (0.5 g) of this material was recrystallized twice from methanol to yield the pure title compound, 0.19 g, m.p. 224°–50°C.

EXAMPLE 7

4-Chloro-6-hydroxy-2-(2-propoxyphenyl)pyrimidine a) A stirred solution of 4,6-dihydroxy-2-(2-propoxyphenyl)pyrimidine (21.05 g) and phosphoryl chloride (65.8 g) was heated under reflux for 1.5 hours. Excess phosphoryl chloride was removed under reduced pressure and the residue was added to ice. The resultant mixture was extracted with chloroform (200 ml and 2×100 ml) and the combined chloroform extracts were washed with water, dried.(magnesium sulfate) and evaporated under reduced pressure. The residue was eluted from silica with ether to yield 4,6-dichloro-2-(2-propoxyphenyl)pyrimidine, 20.69 g.

b) A stirred solution of 4,6-dichloro-2-(2-propoxyphenyl) pyrimidine (16.68 g) in concentrated hydrochloric acid (40 ml), n-butanol (80 ml) and water (40 ml) was heated under reflux for 3 hours. The cooled reaction mixture was evaporated under reduced pressure to yield a residue which was washed with water and diethyl ether and recrystallized from isopropanol to yield the title compound, 8.46 g, m.p. 115.5°–116.5° C. A sample (1 g) of this material was recrystallized twice from isopropanol to yield the pure title compound, 0.42 g, m.p. 118°–118.5° C.

EXAMPLE 8

6-Ethylamino-2-(2-propoxyphenyl)pyrimidin-4[3H]-one

4-Chloro-6-hydroxy-2-(2-propoxyphenyl)-pyrimidine (0.66 g) and ethylamine in ethanol (33%, 20 ml) was heated at 90° C. in a pressure vessel for 16 hours. The cooled reaction mixture was evaporated under reduced pressure to yield an oil which solidified on trituration with diethyl ether. The residue was recrystallized from isopropanol:diethyl ether, washed with water and recrystallized from isopropanol:water to yield the title compound, 0.47 g, m.p. 187°–80° C.

EXAMPLE 9

6-Propylamino-2-(2-propoxyphenyl)pyrimidin-4[3H]-one

4-Chloro-6-hydroxy-2-(2-propoxyphenyl)-pyrimidine (0.66 g), n-propylamine (1.8 g) and ethanol (20 ml) was heated at 90° C. in a pressure vessel for 16 hours. The cooled reaction mixture was evaporated under reduced pressure to yield an oil which solidified on washing with water. The residue was recrystallized from isopropanol:water to yield the title compound, 0.56 g, m.p. 172°–3° C.

EXAMPLE 10

6-(2-Hydroxyethylamino)-2-(2-propoxyphenyl)pyrimidin-4[3H]-one

A stirred solution of 4-chloro-6-hydroxy-2-(2-propoxyphenyl)pyrimidine (0.43 g) and ethanolamine (0.3 g) in n-butanol (8 ml) was heated under reflux for 4 hours. The cooled reaction mixture was evaporated under reduced pressure to yield a residue which was washed with diethyl ether and then eluted from silica with chloroform:methanol (gradient elution). The combined fractions containing product were evaporated under reduced pressure to yield a crude product which was recrystallized from isopropanol:diethyl ether to yield the title compound, 0.28 g, m.p. 164.5°–165.5° C.

EXAMPLE 11

6-(3-Hydroxypropylamino)-2-(2-propoxyphenyl)pyrimidin-4[3H]-one

A stirred solution of 4-chloro-6-hydroxy-2-(2-propoxyphenyl)pyrimidine (0.66 g) and 3-amino-1-propanol (0.56 g) in n-propanol was heated under reflux for 16 hours. The cooled reaction mixture was evaporated under reduced pressure to yield an oil which was partitioned between chloroform (20 ml) and water (20 ml). The chloroform layer was separated from the aqueous layer which was extracted with chloroform (2×10 ml) and the combined chloroform layers were washed with water, dried (magnesium sulfate) and evaporated under reduced pressure. The residue was recrystallized from isopropanol:diethyl ether to yield the title compound, 0.54 g, m.p. 147.5°–148.5° C.

EXAMPLE 12

4-Hydroxy-6-methyl-2-(2-propoxyphenyl)pyrimidine

A stirred mixture of ethyl acetoacetate (0.72 g) 2-propoxybenzamidine methanesulfonate (1.45 g) and sodium ethoxide in ethanol (from sodium, 0.34 g, and ethanol, 10 ml) was heated under reflux for 22 hours. The cooled reaction mixture was evaporated under reduced pressure and the residue was dissolved in water. The aqueous solution was acidified with concentrated hydrochloric acid and extracted with chloroform (3×15 ml). The combined chloroform extracts were dried (magnesium sulfate) and evaporated under reduced pressure to yield a residue which was recrystallized from isopropanol:diethyl ether to yield the title compound, 0.65 g, m.p. 109°–110.5° C.

EXAMPLE 13

6-Hydroxy-2-(2-propoxyphenyl)pyrimidine-4-carboxylic acid

A solution of 2-propoxybenzamidine methanesulfonate (2.9 g), 10% sodium hydroxide (4 ml) and ethyl 4-oxalacetate (1.6 g ) in water (8 ml) was stirred at ambient temperature for 42 hours. The reaction mixture was evaporated to dryness to yield a crude product which was washed with dilute hydrochloric acid and water to yield the title compound, 0.82 g, m.p. 179.5°–181.5° C. A sample (0.4 g) was recrystallized from ethanol to yield the pure title compound, 0.24 g, m.p. 184°–5° C.

EXAMPLE 14

Ethyl 6-hydroxy-2-(2-propoxyphenyl)-pyrimidine-4-carboxylate

A stirred solution of 6-hydroxy-2-(2-propoxyphenyl) pyrimidine-4-carboxylic acid (1.06 g) in ethanol and concentrated sulfuric acid (0.5 ml) was heated under reflux for 3 hours. Most of the ethanol was removed under reduced pressure, then ice-water was added to the residue. The mixture was made alkaline (pH 10–11) with sodium carbonate solution and then extracted with chloroform (3×25 ml). The combined chloroform extracts were washed with water, dried (magnesium sulfate) and evaporated under reduced pressure to yield after washing with petroleum ether (b.p. 40°–60° C.) the title compound, 0.85 g, m.p. 135.5–137° C. A sample (0.4 g) was recrystallized from ethanol to yield the pure title compound, 0.22 g, m.p. 137°–8° C.

EXAMPLE 15

6-Hydroxy-2-(2-propoxyphenyl)pyrimidine-4-carboxamide

A solution of ethyl 6-hydroxy-2-(2-propoxyphenyl) pyrimidine-4-carboxylate (0.44 g) in aqueous ammonia solution (20 ml) was stirred in a stoppered flask at ambient temperature for 4 hours and then allowed to stand for 3 days. The reaction mixture was acidified with concentrated hydrochloric acid to precipitate the title compound, 0.46 g, m.p. 232°–4° C. This was recrystallized from ethanol:methanol to yield the pure title compound, 0.32 g, m.p. 233.5°–234.5° C.

EXAMPLE 16

4-Cyano-6-hydroxy-2-(2-propoxyphenyl)pyrimidine

A stirred solution of 6-hydroxy-2-(2-propoxyphenyl) pyrimidine-4-carboxamide (0.50 g) in phosphoryl chloride (16 ml) was heated under reflux for 4 hours and then the reaction mixture was evaporated under reduced pressure to remove excess phosphoryl chloride. Water was added to the residue, which was extracted with chloroform (3×20 ml). The combined extracts were washed with water, dried (magnesium sulfate) and evaporated under reduced pressure to yield an oil which was heated on a steam bath with glacial acetic acid (15 ml) for 4 hours. The cooled reaction mixture was evaporated under reduced pressure to yield a crude product which was combined with further product similarly prepared from 6-hydroxy-2-(2-propoxyphenyl)-pyrimidine-4-carboxamide (0.82 g) and phosphoryl chloride (25 ml). The combined products were eluted from silica with ether:chloroform (9:1) and fractions containing product were combined and evaporated under reduced pressure to yield the title compound, 0.31 g, m.p. 135°–6° C. (from isopropanol/ether).

EXAMPLE 17

2-(2-Propoxyphenyl)-6-(1H-tetrazol-5-yl)pyrimid-4(3H)-one

A stirred solution of 4-cyano-6-hydroxy-2-(2-propoxyphenyl)pyrimidine (325 mg), sodium azide (91 mg) and ammonium chloride (75 mg) in dimethylformamide (15 ml) was heated at 125° C. for 5 hours. Most of the dimethylformamide was removed under reduced pressure and water added to the oily residue which solidified. The mixture was cooled and the solid was collected, washed with water and recrystallized from glacial acetic acid to yield the title compound, 174 mg, m.p. 219°–221° C.

EXAMPLE 18

4-Ethyl-6-hydroxy-2-(2-propoxyphenyl)pyrimidine

A solution of ethyl propionylacetate (0.79 g), 2-propoxybenzamidine methanesulfonate (1.45 g) and sodium hydroxide (0.60 g) in water (5 ml) and ethanol (5 ml) was stirred at ambient temperature for 22 hours. Most of the solvent was removed under reduced pressure and water (20 ml) was added. The mixture was acidified to pH 2 with concentrated hydrochloric acid and then extracted with chloroform (3×30 ml). The combined extracts were washed with dilute acetic acid, dried (magnesium sulfate) and evaporated under reduced pressure to yield a residue which was recrystallized twice from ether to yield the title compound, 373 mg. m.p. 97°–98.5° C.

EXAMPLE 19

4-Hydroxy-6-phenyl-2-(2-propoxyphenyl)pyrimidine

In a manner similar to that of Example 18, 2-propoxybenzamidine methanesulfonate (1.45 g) and ethyl benzoylacetate (1.19 g) yielded the title compound, 0.49 g, m.p. 163°–164.5° C. (from isopropanol).

EXAMPLE 20

N-Methyl 6-hydroxy-2-(2-propoxyphenyl)pyrimidine-4-carboxamide

A solution of ethyl 6-hydroxy-2-(2-propoxyphenyl) pyrimidine-4-carboxylate (0.40 g) and methylamine in industrial methylated spirit (33%, 15 ml) in ethanol (15 ml) was stirred at ambient temperature for 6 hours and then allowed to stand for 3 days. The reaction mixture was evaporated under reduced pressure to yield a crude product which was recrystallized from ethanol to yield the title compound, 0.26 g, m.p. 165°–6° C.

EXAMPLE 21

N-Ethyl 6-hydroxy-2-(2-propoxyphenyl)pyrimidine-4-carboxamide

In a manner similar to that of Example 20, ethyl 6-hydroxy-2-(2-propoxyphenyl)pyrimidine-4-carboxylate (0.4 g) and ethylamine in ethanol (33%, 15 ml) yielded the title compound, 0.31 g, m.p. 182.5°–183.5° C.

EXAMPLE 22

N-Propyl 6-hydroxy-2-(2-propoxyphenyl)pyrimidine-4-carboxamide

In a manner similar to that of Example 20, ethyl 6-hydroxy-2-(2-propoxyphenyl)pyrimidine-4-carboxylate (0.40 g), propylamine (5 ml) and ethanol (10 ml) yielded the title compound, 0.3,5 g, m.p. 194.5° C. (from isopropanol).

EXAMPLE 23

6-Ethoxy-2-(2-propoxyphenyl)pyrimidin-4(3H)-one

A stirred solution of 4-chloro-6-hydroxy-2-(2-propoxyphenyl)pyrimidine (0.5 g) and sodium ethoxide (from 0.18 g sodium) in ethanol (25 ml) was heated in a pressure vessel at 125° C. for 24 hours. The residue left after evaporation was dissolved in water (20 ml), acetic acid was added to precipitate a gum, and the mixture was extracted with chloroform. Evaporation of the extract gave a solid which was recrystallized from ether to yield the title compound, 0.07 g, m.p. 95.5°–97° C.

EXAMPLE 24

6-N,N-Bis-(2-hydroxyethyl)amino-2-(2-propoxyphenyl)-pyrimidin-4(3H)-one

A stirred solution of 4-chloro-6-hydroxy-2(2-propoxyphenyl)pyrimidine (0.32 g) and diethanolamine (0.4 g) in 1-propanol (8 ml) was heated under reflux for 17 hours. The residue left after evaporation was purified by flash chromatography (silica, 5% methanol in chloroform) and the major product was recrystallized from 2-propanol to yield the title compound, 0.16 g, m.p. 111°–112° C.

EXAMPLE 25

Pharmaceutical compositions for oral administration are prepared by combining the following:

|  | % w/w |  |  |
| --- | --- | --- | --- |
| 6-N-methylureido-2-(2-propoxyphenyl)-pyrimidin-4[3H]-one | 0.5 | 3.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulations are then filled into individual soft gelatin capsules.

EXAMPLE 26

A pharmaceutical composition for parenteral administration is prepared by dissolving the title compound of Example 15 (0.02 g) in polyethylene glycol 300 (25 ml) with heating. This solution is then diluted with water for injections Ph. Eur. (to 100 ml). The solution is then sterilized by filtration through a 0.22 micron membrane filter and sealed in sterile containers.

EXAMPLE 27

1,6-Dihydro-6-oxo-2-(2-ethoxyphenyl)pyrimidine-5-N-(1H-tetrazol-5-yl)carboxamide A slurry of N,N-carbonyldiimidazole (3.24 g., 0.02 mole) in tetrahydrofuran (20 ml) was added to a stirred suspension of 1,6-dihydro-6-oxo-2-(2-ethoxyphenyl)-pyrimidine-5-carboxylic acid (2.60 g., 0.01 mole) in tetrahydrofuran (40 ml). The mixture was stirred under reflux for 16 hours. The solvent was removed. A mixture of the residual solid and 5-aminotetrazole (1.03 g., 0.012 mole) in tetrahydrofuran (40 ml.) was heated under reflux for 2 hours. The cooled mixture was filtered, and the collected material (3.3 g.) recrystallized from N,N-dimethylformamide to give a white solid, m.p. 228°–230° C. (decomp). A portion (1.0 g.) of the solid was dissolved in 5% aqueous sodium carbonate. The solution was treated with 6N hydrochloric acid to pH 2. The mixture was filtered and the collected solid washed with water followed by acetone. A slurry of the solid in water (15 ml.) was treated with a few drops of 6N hydrochloric acid, and the mixture was stirred vigorously for 15 minutes. The white solid was collected by filtration, washed with water followed by acetone, and dried to give the title compound, m.p. 284°–285° C.

EXAMPLE 28

Additional compounds similar to the compound of Example 27 may be prepared by following the procedure of Example 27 and using different carboxylic acid derivatives as starting material. These materials and the corresponding compound produced are described more fully in U.S. Pat. No. 4,209,263 to Juby, and are accordingly incorporated herein by reference.

It will be understood that various changes and modifications can be made in the details of procedure, formulation and use without departing from the spirit of the invention, especially as defined in the following claims.

We claim:

1. A method of treating a patient having precancerous lesions sensitive to the compounds below in need of treatment, comprising administering to the patient a pharmacologically effective amount of a compound of the formula:

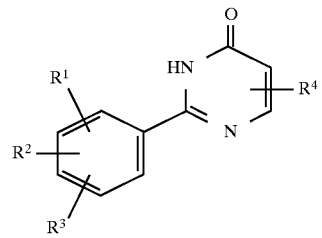

wherein $R^1$, $R^2$ and $R^3$ may be located at any of the available positions on the phenyl ring, each of $R^1$, $R^2$ and $R^3$ may be independently selected from hydrogen, halogen, a lower alkyl group, such as having 1 to 6 carbon atoms, a lower alkoxy, a lower alkenyl, a lower alkenoxy, a lower alkyl thio, a lower alkylamino, a di(lower)alkylamino, a cyano, an acylamino, a carboxyl, a carboalkoxy, a lower alkoxycarbonyl, a lower alkylcarbonyl, a cyclo(lower)alkoxy and cyclo(lower)alkyl (lower)alkoxy in which the ring contains 3 to 8 carbon atoms, preferably 3–6 carbon atoms, a phenyl(lower) alkoxy a nitrogen containing ring, a lower alkylcarbamoyloxy, or a halogen substituted lower alkyloxy group; and $R^4$ may be a lower alkyl, a lower alkoxy, a phenyl, a hydroxy, a halogen, —NHCOR$^5$, —NHCONHR$^6$, 5-tetrazolyl, —CO$_2$R$^7$, a cyano, —CONR$^8$R$^9$, or —NR$^{10}$R$^{11}$, wherein R$^5$ to R$^9$ are independently hydrogen or lower alkyl or R$^9$ may be 5-tetrazolyl, and R$^{10}$ and R$^{11}$ are independently hydrogen or lower alkyl optionally substituted by hydroxy provided that the carbon atom adjacent to the nitrogen atom is not substituted by hydroxy.

2. The method of claim 1 wherein $R^1$, $R^2$ and $R^3$ are independently a hydrogen, a halogen, a lower alkyl, a lower alkenyl, a lower alkoxy, a lower alkenoxy, a phenyl(lower) alkoxy, a cyclo(lower)alkoxy.

3. The method of claim 2 wherein $R^3$ is substituted at position 2 on the phenyl ring.

4. The method of claim 3 wherein $R^1$ and $R^2$ are hydrogen.

5. The method of claim 4 wherein $R^3$ is lower alkoxy, lower alkenoxy, cyclopropylmethoxy or benzoxy.

6. The method of claim 5 wherein $R^3$ is n-propyloxy.

7. The method of claim 1 wherein $R^4$ is a phenyl, a lower alkyl, a hydroxy, a lower alkoxy or —CONR$^8$R$^9$.

8. The method of claim 7 wherein $R^4$ is positioned on the pyrimidinone ring adjacent the oxygen.

9. The method of claim 8 wherein $R^4$ is —$CONR^8R^9$.

10. The method of claim 8 wherein $R^3$ is hydrogen and $R^9$ is 5-1H-tetrazolyl.

11. A method for inhibiting the growth of neoplastic cells sensitive to the compounds below, comprising exposing said cells to an effective amount of a compound of formula:

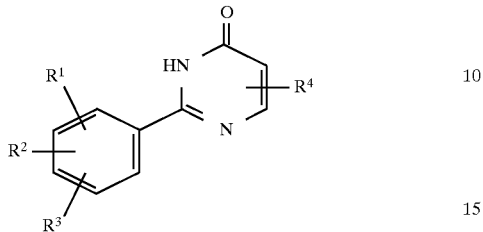

wherein $R^1$, $R^2$ and $R^3$ may be located at any of the available positions on the phenyl ring, each of $R^1$, $R^2$ and $R^3$ may be independently selected from hydrogen, halogen, a lower alkyl group, such as having 1 to 6 carbon atoms, a lower alkoxy, a lower alkenyl, a lower alkenoxy, a lower alkyl thio, a lower alkylamino, a di(lower)alkylamino, a cyano, an acylamino, a carboxyl, a carboalkoxy, a lower alkoxycarbonyl, a lower alkylcarbonyl, a cyclo(lower)alkoxy and cyclo(lower)alkyl (lower)alkoxy in which the ring contains 3 to 8 carbon atoms, preferably 3–6 carbon atoms, a phenyl(lower) alkoxy a nitrogen containing ring, a lower alkylcarbamoyloxy, or a halogen substituted lower alkoxy group; and $R^4$ may be a lower alkyl, a lower alkoxy, a phenyl, a hydroxy, a halogen, —$NHCOR^5$, —$NHCONHR^6$, 5-tetrazolyl, —$CO_2R^7$, a cyano, —$CONR^8R^9$, or —$NR^{10}R^{11}$, wherein $R^5$ to $R^9$ are independently hydrogen or lower alkyl or $R^9$ may be 5-tetrazolyl, and $R^{10}$ and $R^{11}$ are independently hydrogen or lower alkyl optionally substituted by hydroxy provided that the carbon atom adjacent to the nitrogen atom is not substituted by hydroxy.

12. The method of claim 11 wherein $R^1$, $R^2$ and $R^3$ are independently a hydrogen, a halogen, a lower alkyl, a lower alkenyl, a lower alkoxy, a lower alkenyloxy, a phenyl (lower) alkoxy, a cyclo(lower)alkoxy.

13. The method of claim 12 wherein $R^3$ is substituted at position 2 on the phenyl ring, and $R^1$ and $R^2$ are hydrogen.

14. The method of claim 13 wherein $R^3$ is lower alkoxy, lower alkenoxy, cyclopropylmethoxy or benzoxy.

15. The method of claim 11 wherein $R^4$ is a phenyl, a lower alkyl, a hydroxy, a lower alkoxy or —$CONR^8R^9$.

16. The method of claim 15 wherein $R^4$ is positioned on the pyrimidinone ring adjacent the oxygen, $R^4$ is —$CONR^8R^9$, $R^8$ is hydrogen and $R^9$ is 5-1H-tetrazolyl.

* * * * *